United States Patent [19]

Oswald et al.

[11] 3,940,374

[45] *Feb. 24, 1976

[54] SYNTHESIS OF POLYTHIOL POLYMER INTERMEDIATES FROM POLYUNSATURATED HYDROCARBONS

[75] Inventors: Alexis A. Oswald, Mountainside, N.J.; Wolfgang H. Mueller, Karlsruhe, Germany; Daniel N. Hall, Summit, N.J.

[73] Assignee: Exxon Research and Engineering Company, Linden, N.J.

[ * ] Notice: The portion of the term of this patent subsequent to Dec. 7, 1988, has been disclaimed.

[22] Filed: June 18, 1971

[21] Appl. No.: 154,627

Related U.S. Application Data

[62] Division of Ser. No. 665,728, Sept. 6, 1967, Pat. No. 3,625,925.

[52] U.S. Cl. ................. 260/79; 427/340; 427/385; 156/327; 156/330; 428/419; 204/159.18; 260/37 R; 260/47 EC; 260/77.5 CR; 260/79.5 C; 260/609 B; 260/609 R; 260/830 S
[51] Int. Cl.² ........................................ C08G 23/00
[58] Field of Search ............ 260/79, 79.5 R, 79.5 C, 260/609 R, 609 B, 294.8; 204/159.18, 47 EC

[56] References Cited
UNITED STATES PATENTS

| | | | |
|---|---|---|---|
| 3,310,527 | 3/1967 | De Acetis et al. | 260/47 |
| 3,505,166 | 4/1970 | Jones et al. | 260/47 |

*Primary Examiner*—Donald E. Czaja
*Assistant Examiner*—T. Pertilla
*Attorney, Agent, or Firm*—Robert J. Baran

[57] ABSTRACT

Polythiols having more than two terminal and/or pendant thiol groups per polymer molecule are formed by the free radical catalyzed addition of a monomer system made up of either hydrogen sulfide or a dithiol alone or in combination with an acetylenic compound to a polyolefin having at least three olefin sites. The polyolefin is preferably a tri-terminal olefin. The polythiol products are liquid, essentially gel-free materials having number average molecular weights varying from 200 to 30000. The polyfunctional prepolymers of the invention can be cured to stable three-dimensional networks with inexpensive bi-functional oxidants such as lead dioxide. Additionally, prepolymer compositions having 3 or more pendant or terminal thiol groups per molecule when combined with polyfunctional organic reagents, such as diepoxides, form stable, high-tenacity adhesive systems.

8 Claims, No Drawings

SYNTHESIS OF POLYTHIOL POLYMER INTERMEDIATES FROM POLYUNSATURATED HYDROCARBONS

CROSS REFERENCE TO RELATED APPLICATION

This application is a division of U.S. patent application Ser. No. 665,728 filed Sept. 6, 1967; now U.S. Pat. No. 3,625,925.

DETAILED DESCRIPTION

The present invention relates to novel, low molecular weight polythiol prepolymers, a novel free radical addition process for their formation and to cured compositions formed from said polymers. More particularly, the present invention is directed to low molecular weight polythiols formed by the addition of a monomer system made up of either hydrogen sulfide or a dithiol, alone or in combination with an acetylenic compound to a polyolefin having at least three olefinic sites of unsaturation.

The addition of dithiols (dimercaptans) to unsaturated hydrocarbons has been known for some time. For example, Marvel and Chambers, J. Am. Chem. Soc. 70, 993 (1948) and Marvel and Cripps, J. Pol. Sci. 8, 313 (1952) reported the reaction of dithiols with conjugated and non-conjugated diolefins. The polymeric compositions so produced were essentially straight chain materials of relatively low molecular weight having an average of from one to two terminal thiol functions per polymer molecule. Similarly, in copending application Ser. No. 541,696, filed Apr. 11, 1966, the formation of essentially straight chain polythioethers by the addition reaction of dithiols with acetylenic compounds is reported. Such polythioether addition products have a maximum of two terminal thiol substituents per polymer molecule. Because the polythioether polymers of the prior art had a maximum of two terminal and/or pendant thiol functions per polymer molecule, these materials could be crosslinked to stable three-dimensional networks only with the use of relatively expensive polyfunctional reagents. Inexpensive bi-functional curing agents, such as lead dioxide could not be used as such reagents; they merely served to extend the polymer chains and failed to form a stable, rubbery three-dimensional network.

SUMMARY OF THE INVENTION

Now, in accordance with the present invention, it has been found that polythiol polymer intermediates having on the average at least two terminally or pendantly located thiol groups per molecule (hereafter referred to as available thiol sites) can be formed by the free radical addition of a monomer system composed of either hydrogen sulfide or a dithiol, alone or in combination with an acetylenic compound, to a polyolefin having at least three olefin sites, preferably three terminally located sites of unsaturation. With the present system, it is possible to prepare polymers having wide variations in the number of thiol functions per polymer molecule in a given molecular weight range by controlling the amount of polyolefin used. By controlling the amount of polyolefin comonomer in the feed, it is theoretically possible to form polymers in any given molecular weight range with a functionality varying between more than two terminally or pendantly located thiol groups and the theoretical gel point of the polymer. The polythiol polymers of the invention exhibit number average molecular weights varying from about 200 to 30,000. Liquid polymers which find the greatest utility in mastic and adhesive applications have number average molecular weights varying from about 1000 to about 8000.

One class of polythiols is formed by the reaction of a polyolefin with $H_2S$, a dithiol, or mixtures thereof in accordance with the following equation:

$$Q-(CX=CYZ)_a + H(SR_1)_bSH \rightarrow$$
$$(CYZ=CX)_{\overline{a-d}}\, Q-CHX-CYZ-(SR_1)_b-SH]_{a-d}$$

wherein Q is a polyvalent organic radical, $R_1$ is a divalent organic radical, preferably an alkylene radical, having from 1 to 30 carbon atoms; X, Y and Z are either a hydrogen radical or a monovalent organic radical, in particular an alkyl radical, having from 1 to 30 carbon atoms; $a$ varies from 3 to 30; $b$ ranges from 0 to 30; and $d$ varies from 0 to 27.

Polyolefins having terminal vinyl groups are particularly attractive feedstocks in polythiol formation. Their use is demonstrated in the following equation:

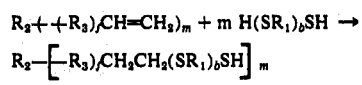

wherein $R_2$ is a polyvalent organic radical having from 1 to 30 carbon atoms; $R_3$ is a divalent hydrocarbon radical preferably an alkylene radical, having from 1 to 10 carbon atoms; $R_1$ and $b$ are as defined above; $f$ is 0 or 1; and $m$ varies from 3 to 10.

Representative, non-limiting reactions and products contemplated by this invention may be represented by the following equations:

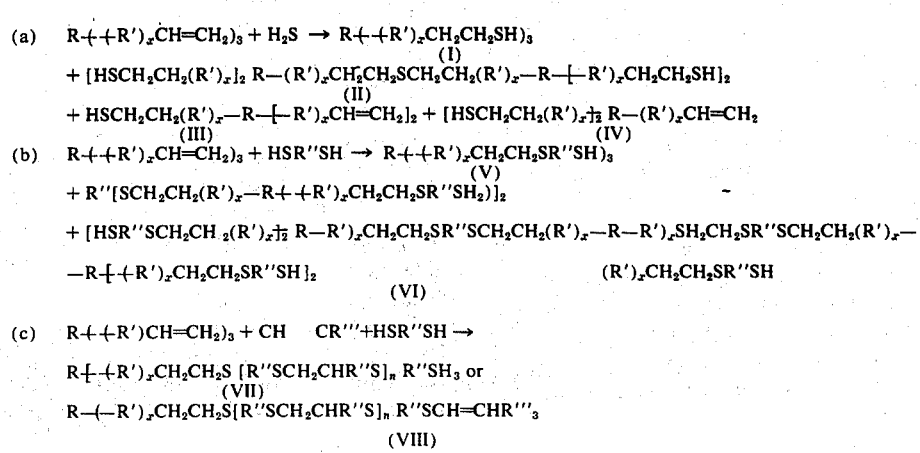

While all of the above equations illustrate reactions involving tri-terminal olefins, it should be recognized that other types of polyolefins having at least three olefin sites can also be used. Equation (a) demonstrates the reaction of a tri-terminal olefin with hydrogen sulfide. The relative proportions of the amounts of products I, II, III, IV, etc. obtained with the reaction of hydrogen sulfide with triolefin is strongly dependent upon the molar ratio of the reactants present in the reaction zone. A very high excess of the hydrogen sulfide results in the formation of low molecular weight trithiol (I) and tetrathiol (II). A small excess of $H_2S$ usually leads to higher molecular weight polythiols and eventually crosslinked products.

Equation (b) illustrates the reaction of a tri-terminal olefin with a dithiol. If a large excess of dithiol is used in the reaction, such as greater than two moles of dithiol per mole of olefin unsaturation, the predominant product obtained is a trithiol (V). If smaller amounts of dithiol are used in combination with the tri-terminal olefin again high molecular weight polythiols are formed in the case of high reactant conversion. If R'' is a divalent hydrocarbon radical having an excess of 12 carbon atoms or if the thiol group of the dithiol is attached to a secondary carbon atom, the reaction proceeds at a much slower rate.

Equation (c) illustrates a co-addition reaction of a tri-terminal olefin with an acetylenic compound and a dithiol. Again, whether or not products VII and VIII are obtained in substantial yield is dependent upon whether the molar ratio of dithiol to tri-terminal olefin in the reaction zone is maintained at levels above or below about two moles of dithiol per mole of olefin unsaturation present in the reaction zone. The relative molar amounts of acetylenic compound to dithiol compound present in the reaction zone determines the number of repeat units in the polythioether (the value of $n$) and whether or not the polymer will contain terminal olefin or thiol functionality. If the acetylenic compound is present in the reaction zone in excess of the dithiol, the product recovered will contain high levels of terminal olefin functionality. In contrast, if the dithiol is in excess of the acetylenic compound present in the reaction zone, the final product secured will contain predominantly thiol terminal functionality.

Products VII and VIII can also be obtained utilizing sequential reaction techniques as opposed to the co-addition reaction illustrated in Equation (c). For example, the triterminal olefin can be reacted with a large excess of dithiol to form a thiol terminated product. This product can be isolated from the reaction mixture and contacted with a molar excess of the acetylenic compound to form a polythioether product having terminal olefin functionality. This product in turn can also be isolated from the reaction mixture and contacted with an excess molar amount of dithiol to form products whose terminal functionality is primarily composed of thiol groups. Such sequential reactions can be continued until products having the desired molecular weight and terminal or pendant functionality are secured.

Product II of Equation (a) and product VI of Equation (b), because of their high levels of available thiol sites, find particular utility in adhesive applications. Products II and VI, when mixed with crosslinking agents such as di-epoxides and poly-epoxides form excellent adhesive systems that rapidly cure at room temperature conditions. The products of Equation (c), especially product VII, find their greatest utility as the base substituent of mastic compositions. Such materials can be readily crosslinked with diisocyanates, diacrylates, dimaleates, divinyl sulfone, etc. to stable, three-dimensional networks. They can also be cured utilizing inexpensive oxidative curing systems. The value of $n$ as used in products VII and VIII of Equation (c) can vary over a wide range. Generally, $n$ ranges between 1 and 100, preferably between 2 and 30. Products finding the greatest utility as the liquid base constituent for mastic compositions exhibit $n$ values varying from about 3 to 15.

The products of this invention, depending upon their molecular weight, are essentially colorless liquids of varying viscosity or low melting solids. Polythioether-polythiol products which have more than three terminally or pendantly located thiol functions per molecule and which find the greatest utility in adhesive applications exhibit number average molecular weights, as determined by vapor pressure osmometry, varying from 400 to 20000, preferably 500 to 15000. Products having the greatest utility as the base constituent of mastic compositions and which usually have on the average of more than two or three terminally or pendantly located thiol functions per polymer molecule exhibit number average molecular weights, as determined by vapor pressure osmometry, varying from about 800 to 10000, preferably between 1000 and 8000.

The polyolefin utilized as a starting material in the formation of the polymer products of this invention is a polyolefin compound having at least three olefinic sites of unsaturation. Useful polyolefins may have from 7 to 100 carbon atoms, preferaby 8 to 36 carbons atoms, and the olefinic sites of unsaturation may be either conjugated or non-conjugated and can be located either terminally or internally in the polyolefin molecule. As terminal sites of unsaturation are more reactive than internally located olefin sites, it is desirable that the polyolefin utilized as a starting material have at least two terminally located sites of unsaturation. Most preferably, the polyolefin used in a triterminal olefin having the general formula:

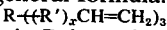
R($(R')_x$CH=CH$_2$)$_3$ wherein R is a trivalent organic radical, particularly a trivalent hydrocarbon radical, having from 1 to 30, preferably 1 to 12, carbon atoms; R' is a divalent radical, preferably an alkylene radical having 1 to 10 carbon atoms; and $x$ is 0 or 1.

Representative examples of useful polyolefins having at least three olefinic sites of unsaturation include: Trivinyl cyclohexane, octatriene, cyclododecatriene, cycloheptatriene, triallyl carbinol, triallylphosphate, trimethylol propane triacrylate, triacryloyl triazin, trivinyl chlorosilane, cyclooctatetraene, tetravinyl silane, dimethyl heptatriene, polybutadiene, etc.

As stated previously, the present polythioetherpolythiol compositions are formed by reacting relatively minor amounts of polyolefins with a monomer system made up of either hydrogen sulfide or dithiol compound alone or in combination with an acetylenic compound. Useful dithiol compounds have the general formula:

HSR''SH wherein R'' is a divalent organic radical, preferably a divalent hydrocarbon radical or a divalent radical containing either sulfur, oxygen or silicon on addition to hydrogen and carbon atoms. Desirably, R'' is (1) a $C_1$–$C_{30}$ divalent alkylene radical, e.g. dimethylene, hexamethylene, etc.; (2) a $C_2$–$C_{30}$ divalent unsaturated alkylene radical such as 2-buten-1,4-ylene, 2-butyne-1,4-ylene, etc.; (3) a $C_8$–$C_{30}$ bix-alkylene substituted aromatic radical, e.g. p-xylylene, p-bis-dimethylene-benzene, etc.; (4) a $C_6$–$C_{30}$ divalent aromatic radical such as m-phenylene, 1,5-naphthylene, etc.; and (5) a $C_2$–$C_{30}$ divalent organic radical containing either sulfur, oxygen or silicon in addition to carbon and hydrogen atoms such as thio-bis-ethylene, oxy-bis-ethylene, thio-bis-trimethylene, thio-bis-ethylthioethylene, dimethyl silane-bis-ethylene, etc.

Particularly preferred thiols are those compositions wherein R'' is a lower alkylene radical such as an alkylene radical having from 2 to 4 carbon atoms as such materials are especially reactive and are readily available at relatively low cost.

Acetylenic compounds are used as the third component in some of the polymer systems of this invention. Applicable acetylenic compounds have the general formula:

$$CH \equiv CR'''$$

wherein R''' is a hydrogen radical or a $C_1$–$C_{30}$ hydrocarbon radical. Preferably, R''' is (1) a hydrogen radical; (2) a $C_1$–$C_{30}$ alkyl group e.g. methyl, ethyl, pentyl, etc.; (3) a $C_2$–$C_{20}$ alkenyl radical such as vinyl, allyl, 3-butenyl, etc.; (4) a $C_2$–$C_{30}$ alkynyl radical, e.g. ethynyl, 4-pentynyl; (5) a $C_7$–$C_{20}$ aralkyl radical such as benzyl, phenylethyl, naphthyl methyl; and (6) a $C_1$–$C_3$ hydroxyalkyl radical such as hydroxymethyl.

Although any of the above-named materials will incorporate into a polymer system made up of a polyolefin and either hydrogen sulfide or a dithiol, it is especially preferred that R''' be a $C_{10}$ radical or lower, especially a $C_1$–$C_4$ alkyl radical. Although mono-substituted acetylenes are preferred for use in the instant invention, acetylene itself and disubstituted acetylenic compounds having the general formula:

$$R'''C \equiv CR'''$$

can also be used either alone on in combination with monosubstituted acetylenic compounds.

A preferred reactant combination is a bis-primary dithiol compound together with trivinyl cyclohexane and methylacetylene. Such a combination leads to a mixture of polythioether dithiols and trithiols as illustrated by the following equations:

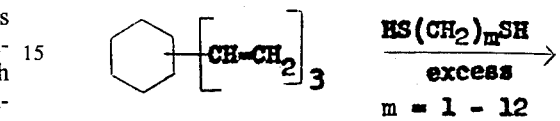

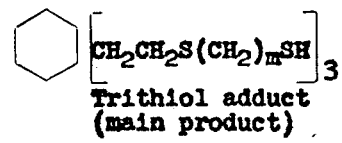

The reaction of trivinyl cyclohexane, and of terminally unsaturated trivinyl compounds in general, with dithiols is faster than that of methylacetylene, and acetylenes in general with dithiols. Consequently, the above trithiol adduct is formed before significant amounts of the acetylene react with the dithiols. Of course this adduct may also be prepared separately in the absence of the acetylene compound.

The trithiol adduct is then reacted with the acetylene and the excess dithiol in an alternating fashion so as to provide a trifunctional polythioether:

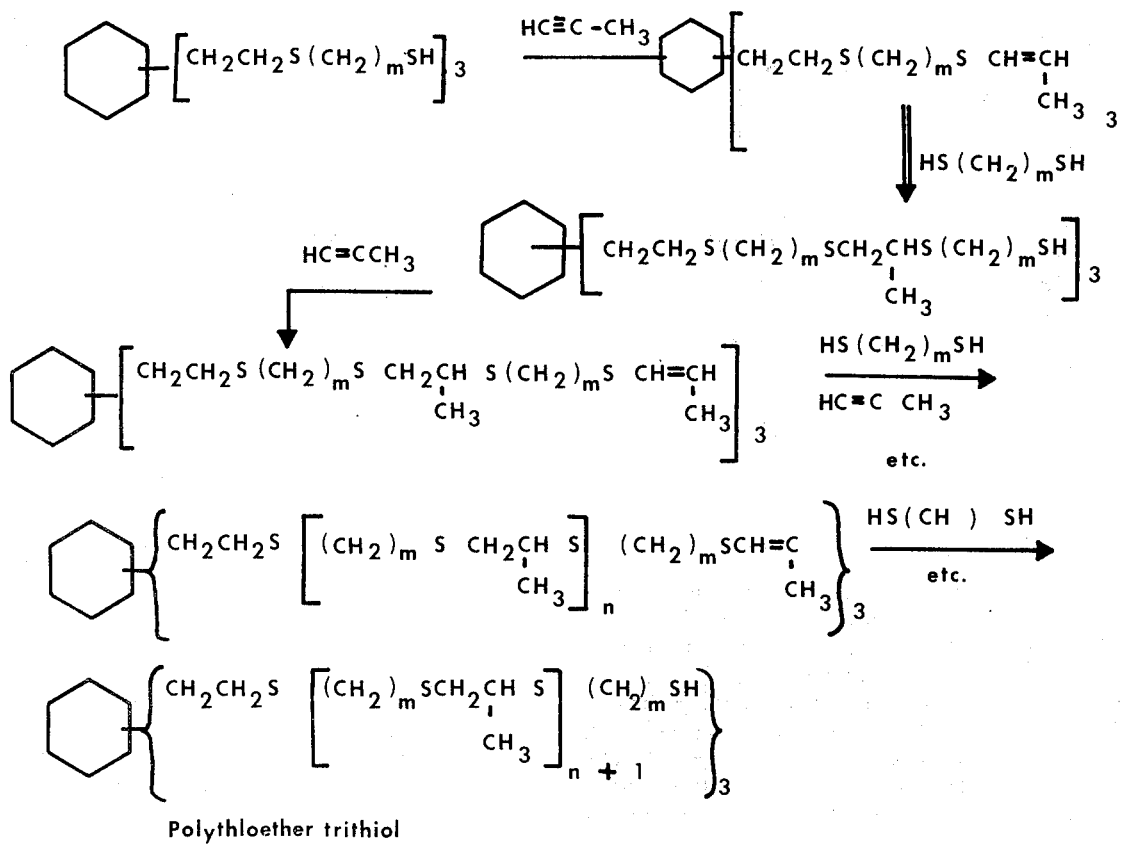

Polythioether trithiol

Concurrent with the above reactions some of the dithiol reacts with methyl acetylene without any trithiol being involved. This leads to difunctional polythioethers:

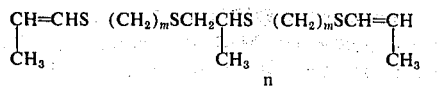

and

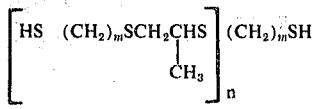

Of course, tetrathiols, pentathiols, etc. that are formed via the reaction of trivinyl cyclohexane with dithiols will also react in the same manner and lead to the corresponding polythioether polythiols.

According to the process of this invention, a polyolefin having at least three olefinic sites of unsaturation is reacted with a monomer system made up of either (1) hydrogen sulfide, (2) a dithiol, (3) hydrogen sulfide and an acetylenic compound, or (4) a dithiol and an acetylenic compound. The ratio of the reactants present in the reaction zone has a strong effect upon the molecular weight of the polymer products and the extent to which the products contain either terminally or pendantly located thiol functionality. In two component systems involving the reaction of either hydrogen sulfide or a dithiol with a polyolefin, at least one mole of either hydrogen sulfide or dithiol should be present in the reaction zone for every mole of olefinic unsaturation present in the reaction zone. It is preferred, however, that at least from three to thirty times the minimum amount of either hydrogen sulfide or dithiol be present during the addition reactions.

If products having more than two terminal or pendantly situated thiol functions are to be obtained from two component reactions at least one mole of $H_2S$ or dithiol should be present in the reaction zone for every mole of unsaturation present in the acetylenic compound and polyolefin. Preferably, from two to ten times the minimum amount of $H_2S$ or dithiol is present in the reaction zone. In the three component reactions, the maximum amount of polyolefin desirably present in the reaction zone varies from 0.1 to 10 mole % of the total reactants. If the polyolefin is present in excess of these levels, the polymer composition obtained at high reactant conversions may be severely gelled.

The process for the production of the polythioetherpolythiol addition products can be carried out in bulk, in the presence of inert solvents, or with the use of water emulsion techniques. Both two and three component reactions can be carried out most efficiently using bulk polymerization techniques, that is, carrying out the addition reaction in the absence of solvents. When higher molecular weight polythioetherpolythiols are desired, the reaction is preferably carried out in the presence of an inert solvent or in a typical water-surfactant emulsion system. When the addition reaction is conducted in the presence of a solvent, the reaction monomers make up from 10 to 95, preferably 50 to 90 weight % of the total monomer-solvent system.

Useful inert solvents include saturated aliphatic hydrocarbons, halogenated saturated aliphatic hydrocarbons, aliphatic ethers, aliphatic thioethers and mixtures thereof. Representative non-limiting examples of such solvents include pentane, cyclohexane, dimethyl sulfide, diethyl sulfide, etc. The use of aromatic hydrocarbons as solvents usually results in sharply reduced reaction rates and undesirable side reactions.

The conditions at which the addition reactions are conducted can vary over a wide range. High yields of polythiols can be obtained for addition reactions carried out in bulk or in solvents at temperatures varying from about $-100°$ to $150°C.$, preferably $-80°$ to $80°C.$, in from five minutes to twelve hours, preferably 10 minutes to 6 hours. When emulsion techniques are utilized, the addition reaction should be conducted at temperatures varying from $-15°$ to $+50°C$ for from 5 minutes to 4 hours.

The addition reactions are not critically sensitive to pressure. However, the pressure within the reaction zone should be sufficient to maintain the major portion of reactants in the liquid state at the temperatures used for the reaction. In general, pressures varying from one to ten atmospheres, preferably atmospheric pressure, can be used. The gaseous acetylenic compound may be gradually introduced during the reaction. In reaction systems wherein potentially explosive acetylenic compounds are used, it is often desirable to pressurize the reactor with an inert gas such as nitrogen in order to maintain the reaction monomers in the liquid state.

While the instant addition reactions will proceed merely by heating the reagents, it is desirable to employ a free radical initiator to promote the formation of the desired products. Radiation such as ultraviolet light or gamma-radiation alone or in conjunction with the application of heat may be used to promote the addition reactions. For example, a $Co^{60}$ gamma irradiation source emitting 4000 curies may be placed at a 6 centimeter distance from a 2 liter reactor to initiate a polyaddition to effective completion in 4 hours.

Additionally, chemical free radical initiators such as organic peroxides, preferably alkyl peroxides, azo compounds, etc. may be used instead of radiation or in combination with it. Representative examples of useful chemical initiators include p-butyl hydroperoxide, bis-t-butyl peroxide, azo-bis-isobutyronitrile, etc. Generally, only minor quantities of the chemical initiators are necessary to promote the addition reactions. Normally, between 0.05 to 10 mole %, preferably 0.1 to 5 mole %, of chemical initiator is used based upon the number of moles of reactant monomers present in the reaction zone.

The reaction vessel used for the addition reactions contemplated by the invention may be constructed of any material that is inert to the reactants and catalysts used and is further capable of withstanding the operating pressures. Reaction vessels formed of quartz, stainless steel, or glass-lined steel are satisfactory.

Although the polythiol and polythioetherpolythiol products formed with the process of this invention have many uses as intermediates because of the terminally or pendantly located thiol and olefinic functionality present within the polymer molecule, materials having on the average of three or more available thiol sites per polymer molecule find particular utility in adhesive applications. Polythioetherpolythiols and polythiols having on the averge of two or more than two terminally or pendantly located thiol functions per polymer molecule can be used as the base substituent for mastic compositions.

In adhesive applications the polythioetherpolythiols can be advantageously used in combination with polyepoxides and diepoxides. For example, polyether A,

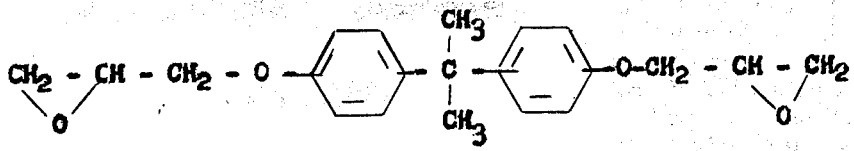

or polyglycidyl ethers,

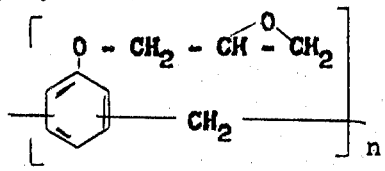

may be used. Trialkylamine compounds serve well as curing catalysts for such combinations. In the presence of catalysts curing usually takes place at room temperature. Curing may be accelerated by heating at temperatures up to 160°C. The polythiol components of such adhesive compositions act as internal flexibilizers. The compositions display excellent adhesion on aluminum, steel, copper, wood, glass, ceramics, plastics, etc.

As stated previously, the polythiol products of this invention having more than two pendantly or terminally located thiol functions per polymer molecule can be readily crosslinked to stable, rubbery three-dimensional networks using inexpensive oxidative curing systems. For example, lead dioxide, zinc peroxide, calcium peroxide may be used as oxidizing agents. Such curing compositions may also contain a curing retarder usually stearic acid. Curing takes place at room temperature in a period ranging from a few hours to several days. Heating of the mixture accelerates curing. Reaction with difunctional reagents such diisocyanates, diepoxides, diacrylates, dimaleates and divinyl sulfone will also result in desirable cured networks.

Prior to curing operations in both adhesives and mastics applications, the polythiol and polythioetherpolythiol products may be compounded with stabilizers, plasticizers, or extender oils and various types of fillers. Up to 200 parts of carbon black, finely divided petroleum coke, or other non-carbon fillers such as titanium oxide, magnesium oxide, silica, etc., may be compounded with 100 parts of the product. The cured mastic compositions are highly resistant to ozone and oxygen degradation and to attack by organic solvents, and organic and inorganic acids and bases. Hence, the cured materials find particular utility in automotive applications.

The invention will be further understood by reference to the following examples.

EXAMPLE 1

Addition of Excess Hydrogen Sulfide to Trivinyl-Cyclohexane

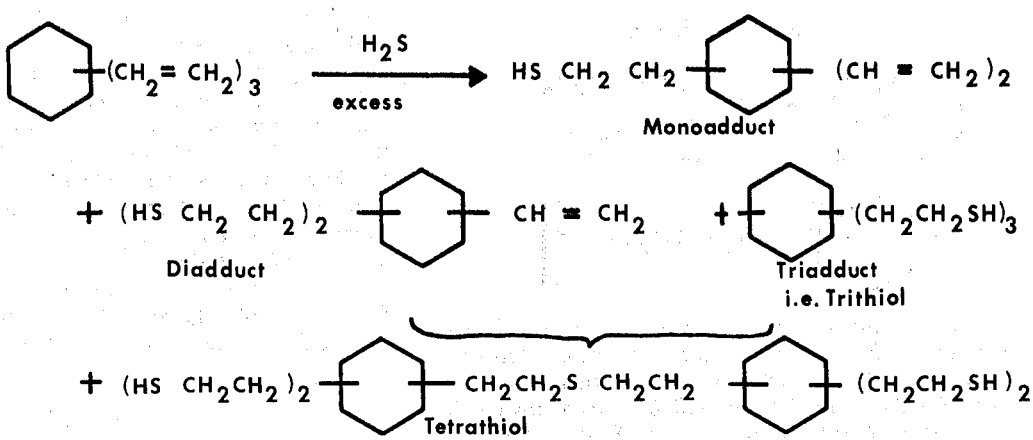

A mixture of 32.4 grams (0.2 moles) of isomeric 1,2,3-, 1,2,4-, and 1,3,5-trivinyl cyclohexanes, containing mainly the 1,2,4-isomer, was placed in a quartz pressure tube equipped with a magnetic stirrer and a Teflon screw valve. The tube was evacuated and 109 grams (3.2 moles) of hydrogen sulfide was condensed in the tube with the triolefin. The tube was then closed, stirring commenced and the reactants radiated with a 75 watt Hanau ultraviolet immersion lamp having a high pressure, wide spectrum mercury arc. Radiation was continued for 24 hours during which time the reactants were maintained at a temperature of about 16°C. Following completion of the reaction period, excess hydrogen sulfide was vented from the tube and the product distilled at 100°C. at pressure of about 0.25 millimeters of mercury. The distillation residue consisted of 48 grams of a colorless liquid product. This product was then heated to 170°C. at a pressure of about $1.5 \times 10^{-3}$ millimeters of mercury pressure to yield 3 grams of an overhead distillate fraction boiling between 105°–120°C. The nuclear magnetic resonance (NMR) spectrum of this overhead fraction exhibited the ratio of olefinic versus total hydrogen characteristic of the monoadduct shown in the reaction scheme. The nuclear magnetic resonance spectrum of the residue indicated that no vinylic protons were present. The number averge molecular weight of the second distillation residue as determined by vapor pressure osmometry at 37°C. in a benzene solution containing 2.4 wt. % residue was 471.

From the nuclear magnetic resonance spectrum and molecular weight evidence, the residual product of the second distillation was believed to have the structural formula of the tetrathiol given in the reaction scheme. The calculated composition of the tetrathiol is 58.24 wt. % carbon, 9.36 wt. % hydrogen, and 32.4 wt. % sulfur. An elemental analysis of the residue of the second distillation indicated that the composition consisted of 58.79 wt. % carbon, 9.40 wt. % hydrogen and 31.81 wt. % sulfur. The calculated number of thiol groups per molecule for the tetrathiol is of course four. The found number of thiol groups per molecule, i.e. thiol functionality by the Zerewitinoff method for the residue was 3.9. Therefore the major component of the residual polythiol is assumed to be the tetrathiol although minor quantities of the other thiolic products indicated in the reaction scheme may be also present.

EXAMPLE 2

Addition of Excess Tetramethylenedithiol to Trivinylcyclohexane

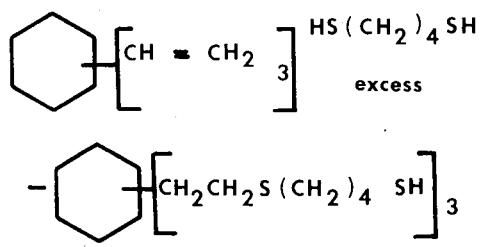

A stirred mixture of 16.2 grams (0.1 mole) of trivinylcyclohexane and 73.2 grams (0.6 mole) tetramethylenedithiol was irradiated with an ultraviolet lamp at 16°C for 24 hours. The unreacted tetramethylenedithiol was removed via distillation by heating the crude product at 135°C at 0.1 millimeter of mercury pressure for 2 hours. The colorless, liquid residual product weighed 50.5 grams, which corresponds to a 95.5% yield calculated for the trithiol of the reaction scheme. The number average molecular weight of the product, as determined by osmometry, was 728. The calculated value for the trithiol is 528. Thiol functionality determination gave a value of 3.1. This data indicates that the major reaction product is the trithiol while a minor amount of tetrathiol is also present.

The calculated composition of the trithiol, $C_{24}H_{48}S_6$, is: C,54.49; H,9.14; S,36.37. The composition of the residual product is C,54.25; H,9.02; S,36.73.

EXAMPLE 3

Addition of Excess Ethanedithiol to Trivinylcyclohexane

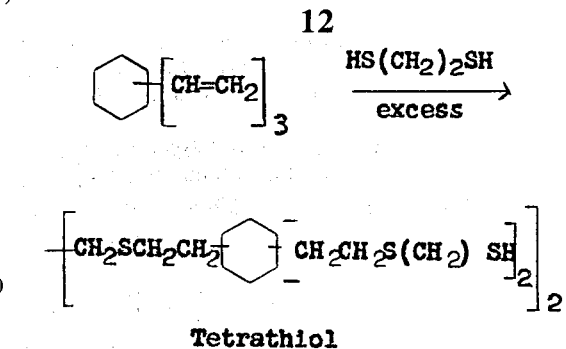

To 235 grams (2.4 moles) of 1,2-ethanedithiol was added 64.8 grams (0.4) moles of trivinylcyclohexane. The mixture was irradiated at 15°C for six hours with ultraviolet light as described in the previous examples. The excess ethanedithiol and other volatiles were then removed from the resulting mixture by heating it at 140° and 0.2 millimeters of mercury pressure. The residual product weighed 153 grams (86% yield of the calculated amount for the tetrathiol). A thiol functionality determination gave a value of 4.1 (Zerewitinoff method). The found molecular weight of the product was 897. The calculated molecular weight for the tetrathiol is 795. The higher than theoretical molecular weight is apparently due to the presence of minor amounts of pentathiol.

The calculated composition for the tetrathiol, $C_{34}H_{66}S_{10}$, is: C,52.69; H,8.56; S,39.08. The found composition of the product is: C,51.34; H,8.36; S,40.30.

EXAMPLE 4

Addition of Excess Trimethylenedithiol to Trivinylcyclohexane

[structure: trivinylcyclohexane + HS(CH₂)₃SH excess → Trithiol → Penthathiol]

Following the procedure of Example 2 a stirred mixture of 81 grams (0.5 moles) of isomeric trivinylcyclohexanes and 162 grams (1.5 moles) of trimethylenedithiol was irradiated with the Hanau immersion lamp at 16°C. for six hours. Following the completion of the reaction period, the unreacted starting materials were removed from the reaction zone by heating the crude product at 140°C. at a pressure of about 0.1 millimeter of mercury. About 190 grams of a colorless liquid was obtained as a residual product. the NMR spectrum of this product indicated that it was substantially free of unsaturation. The number average molecular weight of the products as determined by vapor pressure osmometry at 37°C. in benzene diluent at a polymer concentration of 1.2 grams per 100 cc was 1208. On the basis of the NMR and molecular weight data, the product was believed to have the pentathiol structure given in the reaction scheme. The calculated molecular weight for the pentathiol is 1244. The thiol functionality of the residual product was found to be 4.4.

The calculated composition for the pentathiol, $C_{54}H_{102}S_{12}$, is: C,57.09; H,9.04; S,33.87. The found composition of the product is: C,57.54; H,9.13; S,33.78.

EXAMPLE 5

Addition of Excess Trimethylenedithiol to Cyclododecatriene

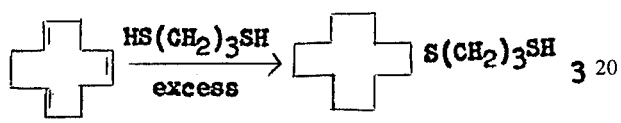

A mixture of 24.3 grams (0.15 mole) of cyclododecatriene and 97.2 grams (0.9 mole) of trimethylenedithiol was reacted for 24 hours under the conditions of Example 3. After the removal of the excess trimethylenedithiol by distillation in vacuo 68 grams of liquid residual product was obtained. This corresponds to a 93% yield of the trithiol based on the above reaction. The thiol functionality of the product was 2.8. The molecular weight of the product was found to be 486 while the calculated molecular weight for the trithiol is 557.

EXAMPLE 6

Co-reaction of Trivinyl-Cyclohexane and Methylacetylene with Trimethylenedithiol in a Pressure Reactor

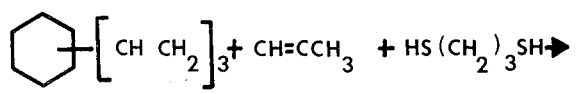

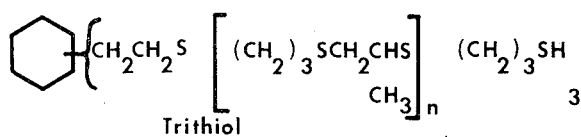

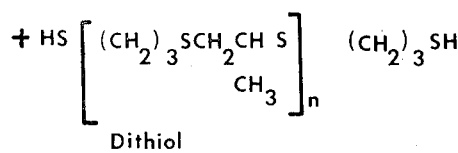

A mixture of 4 grams (0.03 mole) of trivinylcyclohexane, 40.2 grams (1.005 moles) of methylacetylene and 108 grams (1 mole) trimethylenedithiol was irradiated with ultraviolet light in a quartz pressure tube at 16°C for 4 hours. The mixture was thoroughly mixed every half hour by shaking. By the end of the four hours reaction period a very viscous but homogeneous, clear colorless liquid reaction mixture was obtained. One hundred and seventeen grams of the crude product were heated at 150°C under 0.7 millimeters of mercury pressure to remove all the volatile compounds. The residual product weighed 110 grams and was unchanged in appearance. An NMR analysis of the distillate showed that it was free from significant quantities of trivinylcyclohexane. The NMR spectrum of the product did not show any vinylic proton signals indicating the absence of any significant unsaturation. An osmometric molecular weight determination gave a value of 2670. Thiol functionality by the Zerewitinoff method was 2.3 indicating that the product was a mixture of polythioether trithiol and dithiol as shown by the above reaction scheme.

EXAMPLE 7

Co-reaction of Trimethylenedithiol Trivinyl-Cyclohexane and Methylacetylene at Atmospheric Pressure with Gamma Ray Initiation An airtight reactor equipped with an effective, high speed stirrer, a dropping funnel and a filtered glass gas inductor was charged with 324 grams (3 moles) of trimethylenedithiol under nitrogen. Then 12.2 grams (0.075 mole) of trivinylcyclohexane was added with stirring dropwise over a one-hour period to the stirred dithiol. During the addition, the mixture was subjected to gamma irradiation from a 4500 Curie intensity $Co^{60}$ source positioned 7 centimeters from the reactor. Thereafter the reactor was evacuated and filled with methylacetylene by introducing the same under the surface of the liquid mixture. Irradiation was continued during the period of methylacetylene addition. The feeding of methylacetylene into the stirred and irradiated mixture was continued at a sufficient rate to maintain atmospheric pressure within the reactor at 35°–40°C. In this manner 107 grams (2.7 moles) of methylacetylene was added to the reaction mixture in 200 minutes. To complete the reaction, the mixture was irradiated for an additional 120 minutes period after the completion of the addition of the methylacetylene. The resulting colorless, viscous polymer was stripped at 0.2 millimeter of mercury pressure with nitrogen at 125°C for 3 hours. Stripping removed 1.5 weight % of the crude product as a distillate. N.m.r. analysis showed that the residue was a mixture of the expected polythioether dithiol and trithiol. The osmometric molecular weight of the product was found to be 2570. Its thiol functionality was 2.4.

EXAMPLE 8

Co-reaction of Trimethylenedithiol, Trivinyl-Cyclohexane and Methylacetylene at Atmospheric Pressue with Ultraviolet Light Initiation The reaction was carried out as described in the previous example but with ultraviolet light from three 70 watt high pressure mercury arc lamps serving as the reaction initiator. The resulting residual product has a molecular weight of 2600 and a thiol functionality of 2.3.

EXAMPLE 9

Addition of Excess Ethanedithiol to Triallyl Carbinol

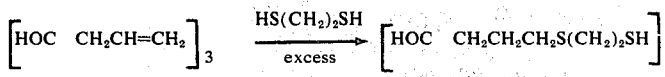

To 56.4 grams (0.6 mole) of ethanedithiol was added dropwise with stirring 15.2 grams (0.1 mole) of triallyl carbinol. The addition was completed in 30 minutes. During addition, the mixture was maintained at 15°C and was irradiated with a U.V. lamp. An additional hour of irradiation after completion of the addition resulted in the essential complete reaction of the triallyl compound. After a total of 10 hours of irradiation the excess dithiol was removed by heating the mixture to 90°C at 0.1 millimeter of mercury pressure. The residual product consisted of 40 grams of a colorless liquid. This corresponds to a 92% yield of the trithiol adduct as shown by the reaction scheme.

EXAMPLE 10

Co-reaction of Triallyl Carbinol and Methylacetylene with Ethanedithiol

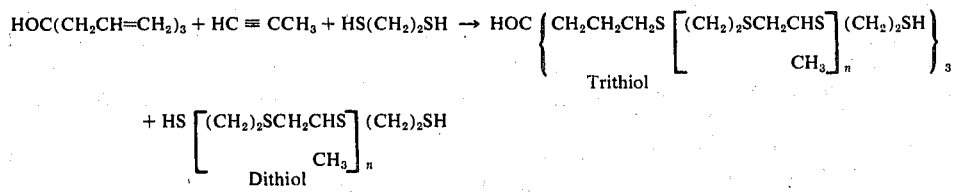

A mixture of 38 grams (0.025 mole) of triallyl carbinol, 20 grams (0.5 mole) of methylacetylene and 51.7 grams (0.55 mole) of ethanedithiol was subjected to U.V. radiation at 15°C for 19 hours. The resulting viscous, liquid product was then heated to 125°C at 0.1 millimeter of mercury pressure for two hours to remove all the volatile components and to obtain 68 grams (90%) of residue consisting of the expected polythioether dithiol and trithiol.

EXAMPLE 11

Co-reaction of Trimethylolpropane Triacrylate and Methylacetylene with Ethanedithiol

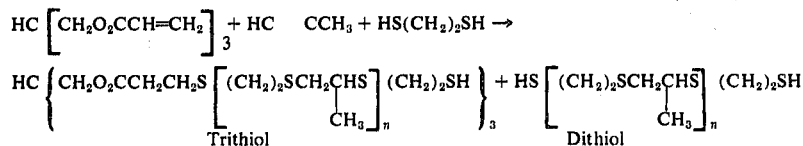

A mixture of 15.5 grams (0.05 mole) of trimethylolpropane triacrylate, 20 grams (0.5 mole) of methylacetylene and 51.7 grams (0.55 mole) of ethanedithiol was reacted as described in Example 2 for 6 hours to yield 74 grams (85%) of a residual product consisting of the expected mixture of polythioether dithiol and trithiol.

EXAMPLE 12

Oxidative Curing of Polythioethers Having a Thiol Functionality Greater Than Two

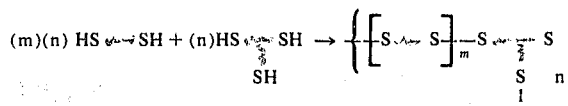

The tetrathiol product of Example 4 and the di- and trithiol mixture of Example 5 were compounded with an oxidative curing composition containing 50 percent of lead dioxide as an oxidizer. The composition also contained 5% stearic acid as a retarder and 45% dibutylphthalate as a plasticizer. Carbon black (Thermax brand) was also added as a filler. Each of the mixtures contained 5 grams of prepolymer, 2 grams of curing composition, and 2.5 grams carbon black, The mixtures were cured at room temperature in a desiccator containing a saturated aqueous solution of potassium thiocyanate. It was observed that tetrathiol was cured to a rubbery composition within 12 hours. The complete curing of the dithiol-trithiol mixture took 36 hours. The latter network showed a higher elongation than the one derived from the tetrathiol. The curing of both residual products could be accelerated by heating.

EXAMPLE 13

Epoxide Curing of Trivinylcyclohexane Derived Polythiols with Diepoxide

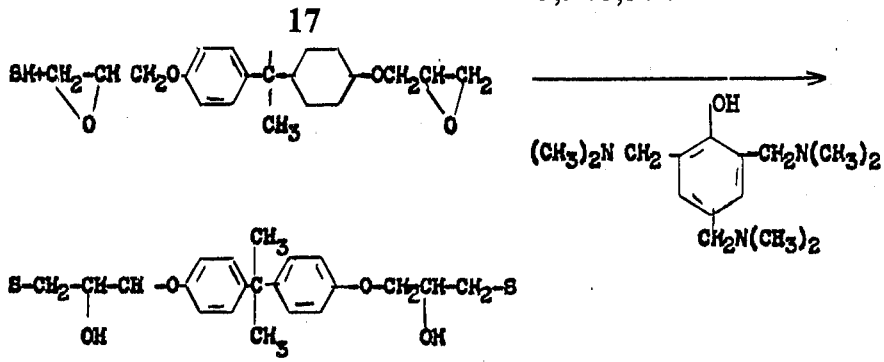

One part by weight of each of the polythiols derived from the experiments described in Examples 1, 3 and 4 was mixed with 2 parts by weight of the diepoxide crosslinking agent, Bis-phenol A di-glycidyl ether, and 0.1 part by weight of the tertiary amine curing catalyst tris-2,4,6-dimethylaminomethylphenol. An exothermic reaction started on mixing. The mixtures were applied to stainless steel strips. Two strips were used for each adhesive composition. The strips were overlapped with the area of overlap being 0.5 square inch.

After three days the strips were pulled apart at a rate of 0.05 inch per second. The maximum shear force was determined by the shear lap test (ASTM D-1002). The results are tabulated below:

TABLE I

| Polythiol from Example | Polythiol Mol. Weight | Polythiol SH Functionality | Lap Shear Lbs. per in.$^2$ | Apparent Curing Time Min. at 25°C |
|---|---|---|---|---|
| 1 | 471 | 3.9 | 466 | 5 |
| 3 | 897 | 4.1 | 784 | 10 |
| 4 | 1208 | 4.4 | 960 | 60 |

The data show that the polythiols of this invention are cured by the diepoxide at room temperature to give good steel to steel adhesion. Polythioether polythiols of increasing molecular weight display better adhesion but slower cure.

The polythiol-diepoxide compositions were also found to show good adhesion to wood, aluminum, Plexiglass and glass. As such they are useful as general adhesives.

Having thus described the general nature and specific embodiments of the present invention, the true scope of the invention is now pointed out by the appended claims.

We claim:

1. A polythiol composition having the general formula: $(CYZ = CX)_d — Q +CHX—CYZ—(SR_1)_b—SH_{a-d}SH)_Q$ is a polyvalent radical selected from the group consisting of trimethylcarbinol, trimethylphosphate, trimethylol propane triformiate, triformoyl triazine, chlorosilane, silane, and cyclohexane radicals, $R_1$ is a radical selected from the group consisting of (1) a $C_1$–$C_{30}$ divalent alkylene radical, (2) a $C_2$–$C_{30}$ divalent unsaturated alkylene radical, (3) a $C_8$–$C_{30}$ bis-alkylene substituted aromatic radical, (4) a $C_6$–$C_{30}$ divalent aromatic radical, and (5) a $C_2$–$C_{30}$ divalent organic radical containing either sulfur, oxygen or silicon in addition to carbon and hydrogen atoms, X, Y and Z are selected from the group consisting of $C_1$ to $C_{30}$ alkyl radicals and hydrogen radicals, $a$ varies from 3 to 4, $b$ ranges from 0 to 30, and $d$ varies from 0 to 1.

2. The composition of claim 1 wherein X, Y and Z are hydrogen radicals.

3. The composition of claim 1 wherein X, Y and Z are alkyl radicals having from 1 to 30 carbon atoms.

4. A polythiol composition having the general formula: $R_2+(R_3)$ $_f Ch_2CH_2(SR_1)_bSH)_m$ wherein $R_1$ is a radical selected from the group consisting of (1) a $C_1$–$C_{30}$ divalent alkylene radical, (2) a $C_2$–$C_{30}$ divalent unsaturated alkylene radical, (3) a $C_8$–$C_{30}$ bis-alkylene substituted aromatic radical, (4) a $C_6$–$C_{30}$ divalent aromatic radical, and (5) a $C_2$–$C_{30}$ divalent organic radical containing either sulfur, oxygen or silicon in addition to carbon and hydrogen atoms, $R_2$ is a polyvalent radical selected from the group consisting of trimethylcarbinol, trimethylphosphate, trimethylol propane triformiate, triformoyl triazine, chlorosilane, silane, and cyclohexane radicals, $R_3$ is a divalent hydrocarbon radical having from 1 to 10 carbon atoms, $b$ ranges from 0 to 30, $f$ is 0 or 1, and $m$ is 3.

5. The composition of claim 4 wherein $R_1$ is a divalent alkylene radical having from 1 to 30 carbon atoms.

6. A polythiol composition having the general formula: $R+(R')_xCH_2CH_2SH)_3$ wherein R is a polyvalent radical selected from the group consisting of trimethylcarbinol, trimethylphosphate, trimethylol propane triformiate, triformoyl triazine, chlorosilane, silane, and cyclohexane radicals, R' is a divalent alkylene radical having from 1 to 10 carbon atoms, and $x$ varies from 0 to 1.

7. A tetrathiol composition having the general formula $(HSCH_2CH_2(R')_x)_2R—(R')_xCH_2CH_2SCH_2CH_2$-$(R')_x—R—((R')_xCH_2CH_2SH)_2$ wherein R is selected from the group consisting of trimethylcarbinol, trimethylphosphate, trimethylol propane triformiate, triformoyl triazine, chlorosilane, silane, and cyclohexane radicals, R' is a divalent alkylene radical having from 1 to 10 carbon atoms and $x$ varies from 0 to 1.

8. A polythioetherpolythiol composition having the general formula: $R — \{(R')_xCH_2CH_2S(R''SCH_2CHR'''S)_n R''SH\}_3$ wherein R is a radical selected from the group consisting of trimethylcarbinol, trimethylphosphate, trimethylol propane triformiate, triformoyl triazine, chlorosilane, silane, and cyclohexane radicals, R' is a divalent alkylene radical having from 1 to 10 carbon atoms, R'' is selected from the group consisting of (a) a $C_1$ to $C_{30}$ divalent saturated alkylene radical; (b) a $C_2$ to $C_{30}$ divalent unsaturated alkylene radical; (c) a $C_8$ to $C_{30}$ bis-alkylene substituted aromatic radical; (d) a $C_6$ to $C_{30}$ divalent aromatic radical; and (e) a $C_2$ to $C_{30}$ divalent organic radical containing at least one element selected from the group consisting of sulfur, oxygen and silicon in addition to carbon and hydrogen atoms, R''' is selected from the group consisting of (a) a hydrogen radical; (b) a $C_1$ to $C_{30}$ alkyl radical; (c) a $C_2$ to $C_{20}$ alkenyl radical; (d) a $C_2$ to $C_{30}$ alkynyl radical; (e) a $C_7$ to $C_{20}$ aralkyl radical; and (f) a $C_1$ to $C_3$ hydroxyalkyl radical and $n$ varies from 2 to 30, and $x$ ranges from 0 to 1.

* * * * *